United States Patent [19]

Moser et al.

[11] Patent Number: 5,059,683
[45] Date of Patent: Oct. 22, 1991

[54] DYES CONTAINING 6-HYDROXYPYRID-2-ONE GROUPS THE 1-POSITIONS OF WHICH CONTAIN SUBSTITUTED 1,3,5-TRIAZINYL OR PYRIMIDYL-PIPERAZINO OR -PIPERAZINIUM GROUPS LINKED THROUGH BRIDGING RADICALS AND INTERMEDIATES THEREFOR

[75] Inventors: Helmut A. Moser, Oberwil, Switzerland; Roland Wald, Huningue, France

[73] Assignee: Sandoz Ltd., Basel, Switzerland

[21] Appl. No.: 348,340

[22] Filed: May 5, 1989

[30] Foreign Application Priority Data

May 6, 1988 [DE] Fed. Rep. of Germany ....... 3815481

[51] Int. Cl.$^5$ ..................... C09B 29/42; C09B 31/153; C09B 45/14; C09B 45/24
[52] U.S. Cl. ..................... 534/759; 534/606; 534/707; 534/772; 544/196; 544/197; 544/198
[58] Field of Search ............... 534/606, 772, 707, 759; 544/196, 197, 198

[56] References Cited

U.S. PATENT DOCUMENTS

| | | | |
|---|---|---|---|
| 4,213,897 | 7/1980 | Moser et al. | 534/606 |
| 4,273,707 | 6/1981 | Pedrazzi | 534/604 X |
| 4,591,635 | 5/1986 | Greve et al. | 534/606 X |
| 4,594,410 | 6/1986 | Pedrazzi | 534/605 X |
| 4,634,764 | 1/1987 | Greve | 534/606 X |
| 4,665,162 | 5/1987 | Doswald et al. | 534/606 |
| 4,673,735 | 6/1987 | Moser et al. | 534/606 |

FOREIGN PATENT DOCUMENTS

| | | | |
|---|---|---|---|
| 1296857 | 11/1972 | United Kingdom | 534/606 |
| 2173210 | 8/1989 | United Kingdom | 534/606 |

*Primary Examiner*—Floyd D. Higel
*Attorney, Agent, or Firm*—Gerald D. Sharkin; Richard E. Vila; Melvyn M. Kassenoff

[57] ABSTRACT

Compounds of the formula

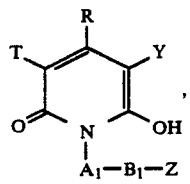

and acid addition salts thereof
wherein
A$_1$ is C$_{1-8}$alkylene; C$_{2-8}$alkylene substituted by 1 or 2 substituents selected from hydroxy, halo and cyano; C$_{2-8}$alkenylene; cyclohexylene; cyclohexylene substituted by 1 to 3 C$_{1-4}$alkyl groups; phenylene or phenylene substituted by 1 or 2 substituents selected from halo, C$_{1-4}$alkyl and C$_{1-4}$alkoxy,
B$_1$ is

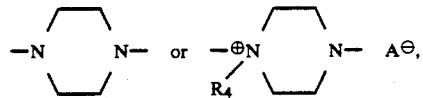

wherein the quaternized nitrogen atom is bound to a carbon atom of A$_1$,
R is hydrogen, C$_{1-4}$alkyl, C$_{5-6}$cycloalkyl, phenyl, benzyl or phenylethyl,
T is hydrogen, cyano, —COOR$_1$, —CON(R$_2$)$_2$, —SO$_2$N(R$_2$)$_2$,

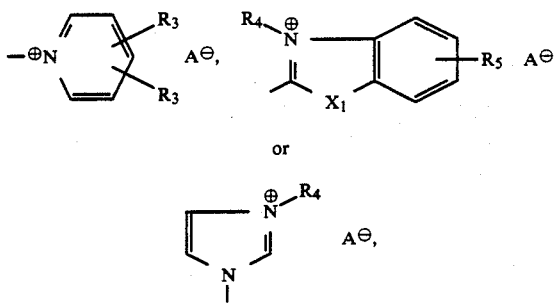

wherein
R$_1$ is C$_{1-6}$alkyl or phenyl(C$_{1-3}$alkyl),
each R$_3$ is independently hydrogen, C$_{1-4}$alkyl, —CON(R$_2$)$_2$ or —N(R$_5$)$_2$, and
X$_1$ is —S—, —O— or —N(R$_5$)—,
Y is hydrogen or a chromophoric group, and
Z is

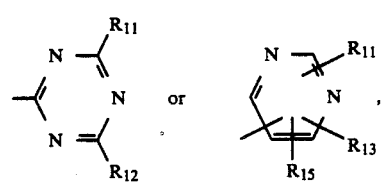

wherein
R$_{11}$ is

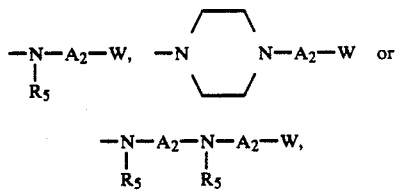

wherein
W is —NR$_6$R$_7$ or —$^\oplus$NR$_8$R$_9$R$_{10}$A$^\ominus$,
R$_{12}$ is (Abstract continued on next page.)

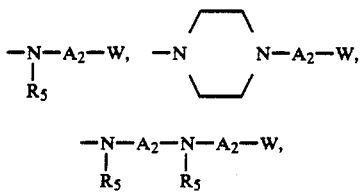

—O—R$_{14}$, —O—A$_2$—O—R$_{14}$ or —NR$_6$R$_7$, wherein

W is as defined above,
R$_{13}$ is hydrogen, halo, C$_{1-4}$alkyl, —O—R$_{14}$, —O—A$_2$—O—R$_{14}$ or —NR$_6$R$_7$, and
R$_{15}$ is hydrogen or halo, with the proviso that the compounds are free of sulfo groups. The compounds wherein Y is other than hydrogen are useful for dyeing and printing substrates such as natural and regenerated cellulose, acid-modified polyamide, leather and paper.

31 Claims, No Drawings

DYES CONTAINING 6-HYDROXYPYRID-2-ONE GROUPS THE 1-POSITIONS OF WHICH CONTAIN SUBSTITUTED 1,3,5-TRIAZINYL OR PYRIMIDYL-PIPERAZINO OR -PIPERAZINIUM GROUPS LINKED THROUGH BRIDGING RADICALS AND INTERMEDIATES THEREFOR

The invention relates to sulphonic acid group-free free basic compounds useful for dyeing substrates such as paper textile and leather.

According to the invention there are provided compounds of formula I

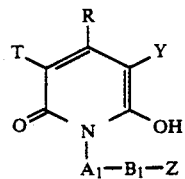
I in free base or acid addition salt form, which compounds are in metal-free or metal complex form,
in which R is hydrogen, $C_{1-4}$alkyl, $C_{5-6}$cycloalkyl, phenyl, benzyl or phenylethyl,
T is hydrogen, —CN, —COOR$_1$, —CON(R$_2$)$_2$, —SO$_2$N(R$_2$)$_2$,

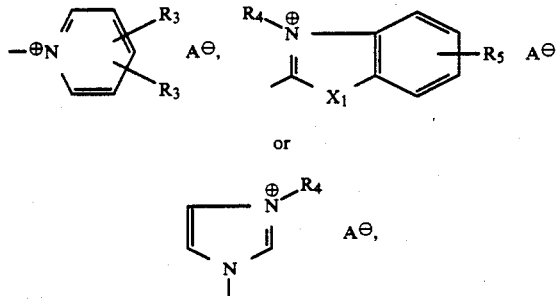

$R_1$ is $C_{1-6}$alkyl or phenyl($C_{1-3}$alkyl),
each $R_2$, independently, is hydrogen or $C_{1-4}$alkyl, or —N(R$_2$)$_2$ is an unsubstituted saturated ring containing 1 to 3 hetero atoms or a saturated rin containing 1 to 3 hetero atoms which ring is substituted by 1 to 3 $C_{1-04}$alkyl groups,
each $R_3$, independently, is hydrogen, $C_{1-4}$alkyl, —CON(R$_2$)$_2$ or —N(R$_5$)$_2$,
each $R_4$, independently, is $C_{1-4}$alkyl,
each $R_5$, independently, is hydrogen or $C_{1-4}$alkyl,
$X_1$ is —S—, —O— or —NR$_5$, and
each $A^\ominus$, independently is a non-chromophoric anion;
Y is hydrogen, —N=N—D or —X—F,
D is the radical of a diazo component,
X is a divalent group, and
F is a chromophoric radical;
$A_1$ is unsubstituted $C_{1-8}$alkylene or $C_{2-8}$alkylene which is substituted by 1 or 2 substituents selected from hydroxy, halogen and cyano; $C_{2-8}$alkenylene; cyclohexylene which is unsubstitu:ed or substituted by 1 to 3 $C_{1-4}$alkyl groups; or phenylene which is unsubstituted or substituted by 1 to 2 substituents selected from halogen, $C_{1-4}$alkyl and $C_{1-4}$alkoxy;
$B_1$ is

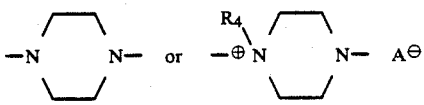

in which the

is bound to a carbon atom of $A_1$;
Z is

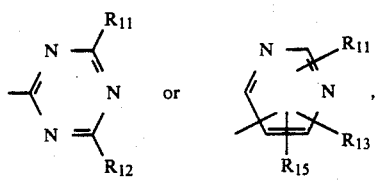

each $R_{11}$ is

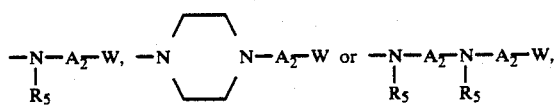

$R_{12}$, independently, has one of the significances of $R_{11}$, or is —OR$_{14}$, —O—A$_2$—OR$_{14}$ or —NR$_6$R$_7$,
$R_{13}$ is hydrogen, halogen, $C_{1-4}$alkyl, —OR$_{14}$, —O—A$_2$—OR$_{14}$ or —NR$_6$R$_7$,
each $R_{14}$, independently, is hydrogen, $C_{4}$alkyl or phenyl,
$R_{15}$ is hydrogen or halogen,
each $A_2$, independently, is $C_{2-8}$alkylene or monohydroxy-substituted $C_{3-8}$alkylene,
each W, independently, is —NR$_6$R$_7$ or —⊕NR$_8$R$_9$R$_{10}$ A$^\ominus$,
each $R_6$, independently, is hydrogen, $C_{1-4}$alkyl, $C_{2-4}$alkyl monosubstituted by hydroxy or $C_{1-4}$alkoxy, cyclohexyl or phenyl($C_{-4}$alkyl),
each $R_7$, independently, is hydrogen, $C_{1-4}$alkyl, $C_{2-4}$alkyl monosubstituted by hydroxy or $C_{1-4}$alkoxy, cyclohexyl, phenyl or phenyl ($C_{1-4}$alkyl), or
—NR$_6$R$_7$ is an unsubstituted saturated ring containing 1 to 3 hetero atoms, a saturated ring containing 1 to 3 hetero atoms which ring is substituted by 1 to 3 $C_{1-4}$alkyl groups, or N'-(amino-$C_{2-3}$alkyl)-piperazino,
each $R_8$ and $R_9$, independently, is $C_{1-4}$alkyl or $C_{2-4}$alkyl monosubstituted by hydroxy or $C_{1-4}$alkoxy,
$R_{10}$ is $C_{1-4}$alkyl or phenyl($C_{1-4}$alkyl), or —⊕NR$_8$R$_9$R$_{10}$ is pyridinium, pyridinium substituted by 1 to 3 $C_{1-4}$alkyl groups, an unsubstituted saturated ring containing 1 to 3 hetero atoms, a saturated ring containing 1 to 3 hetero atoms which ring is substituted by 1 to 3 $C_{1-4}$alkyl groups, or N-$C_{1-4}$alkyl-N'-(amino-$C_{2-3}$alkyl)-piperazinium.

The compounds of formula I, vhether in free base or acid addition salt form, may be in metal-free form or, provided that a metallisable grouping is present, also in metal complex form and are free of sulpho groups and preferably other anionic groups.

In the specification, any halogen means fluorine, chlorine or bromine, especially chlorine.

Unless otherwise indicated, each hetero atom independently is —O—, —S— or —NH—.

Generally, any alkyl, alkylene or alkenylene is linear or branched unless indicated to the contrary.

In any hydroxy- or alkoxy-substituted alkyl or alkylene group which is linked to nitrogen, the hydroxy or alkoxy group is preferably bound to a carbon atom which is not directly attached to nitrogen. In any alkylene group containing two hydroxy groups, the hydroxy groups are bound to different carbon atoms which are preferably in other than an adjacent position. When two oxygen atoms are linked by an alkylene or hydroxyalkylene radical, They are preferably attached to different carbon atoms of the radical.

Any alkyl as R is preferably methyl or ethyl, especially methyl. Any cycloalkyl as R is preferably cyclohexyl.

R is preferably $R_a$, where $R_a$ is methyl, ethyl, cyclohexyl, phenyl or benzyl. More preferably, R is $R_b$ where $R_b$ is methyl, ethyl or phenyl. Most preferably, R is methyl.

$R_1$ is preferably $R_{1a}$, where $R_{1a}$ is $C_{1-4}$alkyl, benzyl or phenylethyl. More preferably, it is $R_{1b}$, where $R_{1b}$ is methyl, ethyl or benzyl.

$R_2$ is preferably $R_{2a}$, where each $R_{2a}$, independently, is hydrogen, methyl or ethyl, or —$N(R_{2a})_2$ is an unsubstituted piperidine, morpholine, piperazine or $N'$-$C_{1-4}$alkylpiperazine ring. More preferably, $R_2$ is $R_{2b}$, where each $R_{2b}$, independently, is hydrogen, methyl or ethyl.

$R_4$ is preferably $R_{4a}$, where each $R_{4a}$, independently, is methyl or ethyl.

$R_5$ is preferably $R_{5a}$, where each $R_{5a}$, independently, is hydrogen, methyl or ethyl.

$X_1$ is preferably $X_{1a}$, where $X_{1a}$ is —O—, —S— or $>NR_{5a}$.

$R_3$ is preferably $R_{3a}$, where each $R_{3a}$, independently, is hydrogen, methyl, ethyl, —$COn(r_{2b})_2$ or —$N(R_{5a})_2$. More preferably, it is $R_{3b}$, where each $R_{3b}$, independently, is hydrogen or methyl.

T is preferably $R_a$, where $T_a$ is hydrogen, —CN, —$COOR_{1b}$, —$CON(R_{2a})_2$ or

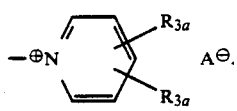

More preferably, T is $T_b$, where $T_b$ is hydrogen, —CN, —$CONH_2$ or

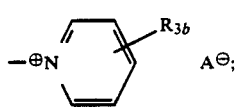

most preferably, T is $T_c$, where $T_c$ is hydrogen, —CN or

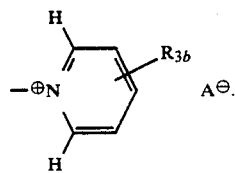

D is preferably the radical of a carbocyclic or heterocyclic aromatic diazo component; more preferably, D is

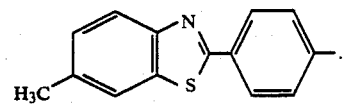

F is preferably the radical of a phthalocyanine, quinophthalone, oxazine, bisoxazine, naphtholactam, di- to tri-phenylmethane, xanthene, indigo, anthraquinone, 5,6-arylo-2-pyrone, nitro or formazan dye, or of an azo dye which is in metal-free or 1:1 or 1:2 metal complex form. More preferably, F is the radical of a phthalocyanine, bisoxazine, anthraquinone or formazan dye or of an azo dye in metal-free or metal complex form.

Most preferably, —X—F is —N=N—$F_a$ in which $F_a$ is the radical of a monoazo, disazo or polyazo dye which is in metal-free or 1:1 or 1:2 metal complex form.

Any alkylene as $A_1$ is preferably $C_{1-6}$alkylene, more preferably $C_{2-3}$alkylene. Any substituted alkylene is preferably monohydroxy-substituted $C_{3-6}$alkylene. Any substituted phenylene as $A_1$ is preferably monosubstituted by chlorine, methyl or methoxy.

$A_1$ is preferably $A_{1a}$, where $A_{1a}$ is unsubstituted $C_{1-6}$alkylene, monohydroxy-substituted $C_{3-6}$alkylene, 1,4-cyclohexylene or 1,3- or 1,4-phenylene which is unsubstituted or monosubstituted by chlorine, methyl or methoxy. More preferably $A_1$ is $A_{1b}$, where $A_{1b}$ is $C_{2-3}$alkylene, monohydroxy-substituted $C_{3-4}$alkylene, 1,4-cyclohexylene or 1,3- or 1,4-phenylene. Most preferably $A_1$ is $A_{1c}$, where $A_{1c}$ is $C_{2-3}$alkylene.

$B_1$ is preferably

$A_2$ is preferably $A_{2a}$, where each $A_{2a}$, independently, is $C_{2-4}$alkylene or monohydroxy-substituted $C_{3-4}$alkylene. More preferably $A_2$ is $A_{2b}$, where each $A_{2b}$, independently, is linear $C_{2-3}$alkylene.

$R_6$ is preferably $R_{6a}$, where $R_{6a}$ is hydrogen, methyl, ethyl, $C_{2-3}$alkyl monosubstituted by hydroxy or methoxy, cyclohexyl or phenyl($C_{1-2}$alkyl);

$R_7$ is preferably $R_{7a}$, where $R_{7a}$ is hydrogen, methyl, ethyl, $C_{2-3}$alkyl monosubstituted by hydroxy or methoxy, cyclohexyl, phenyl or phenyl($C_{1-2}$alkyl);

or —$NR_{6a}R_{7a}$ is an unsubstituted piperidine, morpholine, piperazine or $N'$-$C_{1-4}$alkylpiperazine ring or $N'$-(amino($CH_2$)$_t$)-piperazineo, wherein t is 2 or 3.

More preferably $R_6$ is $R_{6b}$ and $R_7$ is $R_{7b}$, where each $R_{6b}$ and $R_{7b}$, independently, is hydrogen, methyl or ethyl. Most preferably, $R_6$ and $R_7$ are both ethyl.

$R_8$ and $R_9$ are preferably $R_{8a}$ and $R_{9a}$, where each $R_{8a}$ and $R_{9a}$, independently, is methyl or ethyl;

$R_{10}$ is preferably $R_{10a}$, where $R_{10a}$ is methyl, ethyl or benzyl; or $-\ominus NR_{8a}R_{9a}R_{10a}$ is a pyridinium, picolinium or lutidinium ring or a group of the formula

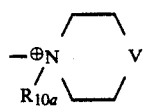

in which V is a direct bond, $-CH_2-$, $-O-$, $-NH-$, $-\underset{|}{N}(C_{1-4}\text{alkyl})$, $-\overset{|}{\underset{|}{\oplus N}}(C_{1-4}\text{alkyl})_2 A\ominus$ or $-\underset{|}{N}(CH_2)_t NH_2$, wherein t is 2 or 3.

More preferably each $R_8$ and $R_9$ is $R_{8b}$ and $R_{9b}$, where each $R_{8b}$ and $R_{9b}$ is methyl or ethyl, and $R_{10}$ is $R_{10b}$, where $R_{10b}$ is methyl, ethyl or benzyl.

W is preferably $W_a$, where $W_a$ is $-NR_{6a}R_{7a}$ or $-\ominus NR_{8a}R_{9a}R_{10a} A\ominus$; more preferably it is $W_b$, where $W_b$ is $-NR_{6b}R_{7b}$ or $-\ominus NR_{8b}R_{9b}R_{10b} A\ominus$. Most preferably W is $-N(\text{ethyl})_2$.

$R_{11}$ is preferably $R_{11a}$, where $R_{11a}$ is

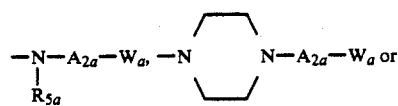

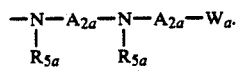

More preferably $R_{11}$ is $R_{11b}$, where $R_{11b}$ is

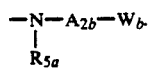

Most preferably $R_{11}$ is $R_{11c}$, where $R_{11c}$ is $-NH-A_{2b}-N(\text{ethyl})_2$.

$R_{14}$ is preferably $R_{14a}$, where $R_{14a}$ is hydrogen, methyl, ethyl or phenyl. More preferably $R_{14}$ is $R_{14b}$, where $R_{14b}$ is hydrogen, methyl or ethyl.

$R_{12}$ is preferably $R_{12a}$, where $R_{12a}$, independently, has one of the significances of $R_{11a}$, or is $-OR_{14a}$, $-O-A_{2b}-OR_{14a}$ or $-NR_{6a}R_{7a}$. More preferably $R_{12}$ is $R_{12b}$, where $R_{12b}$, independently, has one of the significances of $R_{11b}$, or is $-OR_{14b}$, $-O-A_{2b}-OR_{14b}$ or $-NR_{6b}R_{7b}$. Even more preferably $R_{12}$ is $R_{12c}$, where $R_{12c}$, independently, has one of the significances of $R_{11b}$.

Most preferably $R_{11}$ and $R_{12}$ are identical significances of $R_{11b}$, especially identical significances of $R_{11c}$.

$R_{13}$ is preferably $R_{13a}$, where $R_{13a}$ is hydrogen, chlorine, flurine, methyl, $-OR_{14a}$, $-O-A_{2b}-OR_{14b}$ or $-NR_{6b}R_{7b}$.

$R_{15}$ is preferably $R_{15a}$, where $R_{15a}$ is hydrogen, chlorine or fluorine.

Z is preferably $Z_a$, where $A_z$ is

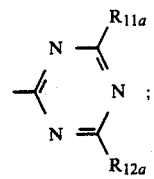

more preferably it is $Z_b$, where $Z_b$ is

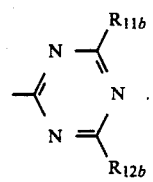

Even more preferably Z is $Z_c$, where $Z_c$ is

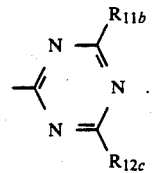

More preferably Z is $Z_d$, where $Z_d$ is

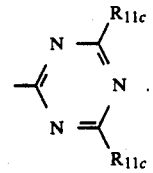

In $Z_c$ $R_{11b}$ and $R_{12c}$ are preferably identical, and in $Z_d$ both $R_{11c}$'s are preferably identical.

Y is preferably $Y_a$, where $Y_a$ is hydrogen or $-N=N-F_b$ in which $F_b$ is a group (a).

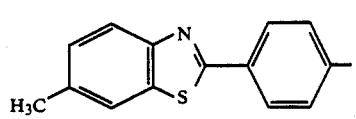

or $F_a$ as defined above.

More preferably Y is $Y_b$, where $Y_b$ is hydrogen or $-N=N-F_c$ in which $F_c$ is a group (a) as defined above or

[Structural formula showing two benzene rings E and E₁ linked by X_o, with R₁₆ substituents, connected via N=N to a pyridone ring system with R_a, T_a, HO, and N-A_{1a}-N-piperazine-N-Z_a]

in which $R_a$, $R_a$, $A_{1a}$ and $Z_a$ are as defined above, each $R_{16}$, independently, is hydrogen, halogen, hydroxy, $C_{1-4}$alkoxy or $C_{1-4}$alkyl, and $X_o$ is as defined below and is attached to the 3- or 4-position of each of rings E and $E_1$.

$X_o$ is a direct bond, —$(CH_2)_p$— in which p is 1 or 2, —CO—, —S—, —O—, —CH=CH—, —$SO_2$—, —NH—, —CONH—, $$-CON-,\ |\ CH_3$$

—$SO_2NH$—, —CONHNHCO—,

[piperazine structure] —N⟨ ⟩N—, [pyrazolone-like structure], —CO—‖O,

[phenylene-CO structure] —CO—⟨ ⟩—CO—, —CON—A_{1c}—NCO—, | | R_{3b} R_{3b}

—CO—N⟨ ⟩N—CO—, —NHCH_2CH_2O—,

—CONHCH_2CHCH_2NHCO—, | OH

—CONH—A_{1c}—OOC—, —NHCONH—,

—SO_2—N⟨ ⟩N—SO_2—,

—SO_2NH—A_{1c}—NHSO_2—, —O—A_{1c}—O— or

—SO_2N—A_{1c}—N—, | | R_{3b} R_{3b} wherein $A_{1c}$ and $R_{3b}$ are as defined above.

More preferably $X_o$ is $X_o'$, where $X_o'$ is —$(CH_2)_p$—, —CONH—,

—CON—A_{1c}—NCO—, —CO—N⟨ ⟩N—CO—, | | R_{3b} R_{3b}

-continued

—CONHCH_2CHCH_2NHCO—, —CONH—A_{2b}—OOC—, | OH

—SO_2—N⟨ ⟩N—SO_2— or —$SO_2NH$—$A_{2b}$—$NHSO_2$—, wherein $A_{2b}$ is as defined above.

Most preferably $X_o$ is $X_o''$ is —$(CH_2)_p$—, —CONH— or

—CON—A_{2b}—NCO—. | | R_{3b} R_{3b}

Preferred compounds correspond to formula Ia,

[Pyridone structure with T_a, R_a, Y_a, =O, OH, N, A_{1a}-N⟨piperazine⟩N-Z_a]      Ia in which the symbols are as defined above.

More preferred are compounds of formula Ia, in which $Y_a$ is $Y_b$ as defined above and in which the $R_a$'s, $A_{1a}$'s and $Z_a$'s, respectively but may be the same or different, and more preferably identical, which compounds are in metal-free or 1:1 or 1:2 metal complex form.

Even more preferred are metal-free compounds corresponding to formula Ib,

[Pyridone structure with T_b, R_b, Y_c, =O, OH, N, A_{1b}-N⟨piperazine⟩N-Z_b]      Ib in which $Y_c$ is hydrogen or —N=N—$F_d$, wherein $F_d$ is a group (a) as defined above or

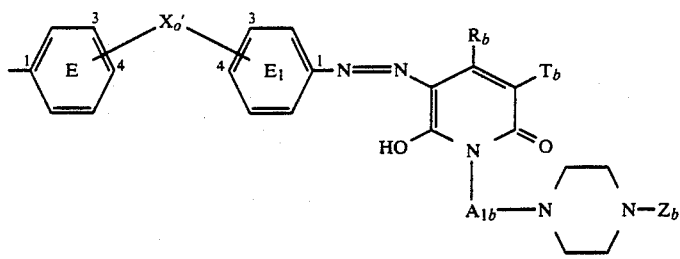

in which $X_o'$ is as defined above and is attached to the 3- or 4-position of ring E and to the 3- or 4-position of ring $E_1$, and the $R_b$'s $T_b$'s, $A_{1b}$'s and $Z_b$'s, respectively, which are as defined above may be the same or different and are preferably identical.

Particularly preferred are metal-free compounds of formula Ib in which
(1) each $R_b$ is methyl;
(2) each $T_b$, independently, is $T_c$;
(3) each $A_{1b}$, independently, is $Z_c$;
(5) those of (1) to (4) corresponding to formula Ic,

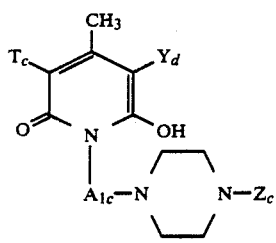   Ic in which $Y_d$ is hydrogen or $-N=N-F_o$ in which $F_o$ is a group (a) as defined above or

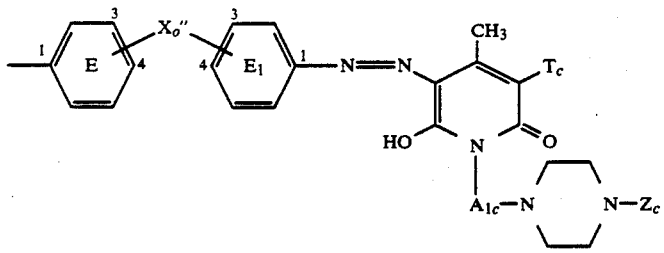

wherein $X_o''$ is as defined above and is attached to the 3- or 4-position of ring E and to the 3- or 4-position of ring $E_1$, and the remaining symbols are as defined above;
(6) those of (5) in which each $Z_c$, independently, is $Z_d$ as defined above;
(7) those of (6) in which the $T_c$'s, $A_{1c}$'s, respectively, are identical.

Preferred compounds of formula I in metal complex form correspond, in 1:1 metal complex form, to formula II,

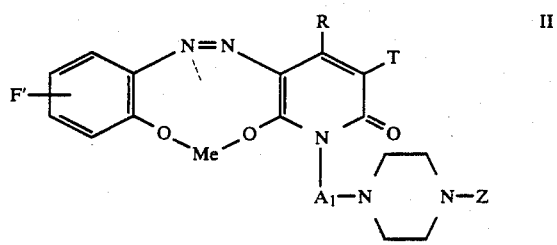   II in which

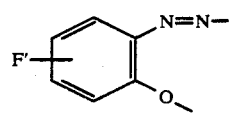

ps signifies F—X— and
Me is a copper, chromium, cobalt, iron, nickel or manganese atom for a 1:1 metal complex, preferably a copper atom.

Further, according to the invention there are provided 1:2 metal complexes of a 1:1 metal complex of formula II wherein Me is chromium, cobalt or iron, with a metal-free compound of formula I or any azo compound which may be converted into a 1:2 metal complex.

Further, according to the invention there is provided a process for the production of a compound of formula I in which Y is hydrogen, comprising reacting a compound of formula III

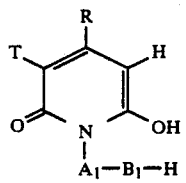   III with a compound of formula IVa or IVb

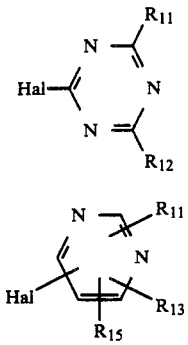

in which Hal is halogen.

Azo compounds of formula I may be prepared by coupling a compound of formula I in which Y is hydrogen with the diazonium salt of an amine of formula VA or Vb

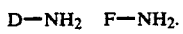

Compounds of formula I in which Y is other than hydrogen or —N=N—D and —X—F is other than —N=F may be prepared by reacting a compound of formula VI

F—M                VI in which M is a functional group capable of reacting with an active hydrogen atom, with a compound of formula I in which Y is hydrogen.

Coupling to form azo compounds of formula I may be carried out according to known methods. Advantageously, coupling is carried out in an aqueous (acid, neutral or alkaline) medium, optionally in the presence of an organic solubilising agent, at a temperature of about $-10°$ C. to room temperature, if necessary, in the presence of a coupling accelerator such as pyridine, urea, etc. Diazotisation is effected by known methods.

The condensation reactions of a compound of formula III with a compound of formula IVa or IVb, or of a compound of formula VI with a compound of formula I is which Y is hydrogen, may be carried out in accordance with known methods.

Compounds of formulae III, IVa, IVb, Va, Vb and VI used as starting compounds are either known, or may be prepared in accordance with known methods.

For example, the compounds of formula III may be prepared according to known methods, by a cyclisation reaction of a compound of the formula T—CH$_2$—CO—NH—A$_1$—B$_1$—H with an alkyl autoacetate of the formula

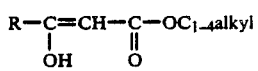

to form a compound of formula III.

The 1:1 metal complexes of formula II may be prepared by metallising a metal-free azo compound of formula I in accordance with known methods with a metal-donating compound which is employed in such an amount to provide at least one equivalent of copper, chromium, cobalt, iron, nickel or manganese per equivalent of monoazo compound to be metallised.

The preferred 1:1 metal complexes, advantageously 1:1 copper complexes, may be prepared by directly reacting a metal-free azo compound of formula I with a metal salt or by oxidative coppering, preferably at 40°–70° C. and at a pH of 4–7, in the presence of copper-(II) salts or with copper powder in the presence of hydrogen peroxide or any other oxidising agent; or preferably demethylating coppering may be applied in a pH range of 3–4 at elevated temperatures.

1:2 Metal complexes of 1:1 complexes of formula II may be obtained in accordance with known methods by metallising a metal-free azo compound of formula I with a metal-donating compound which is employed in such an amount to provide at least one equivalent of chromium, cobalt or iron per two equivalents of a metal-free azo compound of formula I, or by reacting one equivalent of a metal-donatin compound with one equivalent of a metal-free azo compound of formula I and one equivalent of any other azo compound which can be converted into a 1:2 metal complex, or by reacting one equivalent of a 1:1 metal complex of formula II with one equivalent of a metal-free azo compound of formula I or with any other azo compound.

The compounds and complexes of formula I thus obtained may be isolated in accordance with known methods.

In the compounds of formula I, the anions A can be any non-chromophoric anions such as those conventional in basic dyestuff chemisiry. Suitable anions include chloride, bromide, sulphate, bisulphate, methylsulphate, aminosulphonate, perchlorate, benzenesulphonate, oxalate, maleate, acetate, propionate, lactate, succinate, tartrate, malate, methanesulphonate and benzoate as well as complex anions, for example zinc chloride double salts and anions of boric acid, citric acid, glycolic acid, diglycolic acid and adipic acid or addition products of ortho boric acid with polyalcohols with at least one cis diol group present. These anions can be exchanged for each other by ion exchange resins on reaction with acids or salts (for example via the hydroxide or bicarbonate) or according to German Offenlegungsschrift 2,001,748 or 2,001,816.

The metal-free or metal-containing compounds of formula I (preferably in acid addition salt form or quaternary ammonium salt form) in which Y is other than hydrogen are suitable for dyeing, padding or printing fibres, threads or textile materials, particularly natural or regenerated cellulose materials ior example cotton polyester or synthetic polyamides modified by anionic groups.

The dyestuffs of formula I are also used for dyeing, padding or printing fibres, threads or textiles produced therefrom which consist of or contain homo- or mixed polymers of acrylonitrile or of 1,1-dicyanoethylene.

The textile material is dyed, printed or pad-dyed in accordance with known methods. Acid-modified polyamide is dyed particularly advantageously in an aqueous, neutral or acid medium, at temperatures of 60° C. to hoiling point or at temperatures ahove 100° C. under pressure.

Cellulose material is mainly dyed by the exhaust process, i e irom a long or short bath, at room temperature to boiling temperature, optionally under pressure, whereby the ratio of the bath is from 1:1 to 1:100 and preferably from 1:20 to 1:50. If dyeing is effected from a short bath, then the liquor ratio is 1:5 to 1:15. The pH of the dyebath varies between 3 and 10 (for short and long dyebaths).

Printing may be effected in accordance with known methods.

The dyestuffs of formula I are particularly suitable for dyeing or printing paper, e.g. for the production of bulk-dyed, sized and unsized paper. The dyestuffs may similarly be used for dyeing paper by the dipping process. The dyeing of paper is effected by known methods. The compounds of formula I are especially suitable for dyeing ligneous paper, particularly paper with mechanical wood pulp. They may also be applied to bast fibres such as hemp, flax, sisal, jute, coir or straw.

The dyestuffs of formula I are also suitable for dyeing or printing leather by known methods and dyeings with good fastness properties are obtained.

Dyeings prepared with dyestuffs of formula I on paper produce a substantially clear waste liquor which is important for environmental reasons. The dyestuffs of formula I are highly substantive and have good build-up properties. They do not bleed once applied to paper are insensitive to pH, and do not mottle on ligneous paper. Dyeings produced with dyestuffs of formula I have good light fastness and the nuance on exposure for a long time to light fades tone-in-tone. The dyestuffs of formula I have good wet fastness properties and are fast not only to water but also to milk, soap water, sodium chloride solutions, fruit juices, sweetened mineral water and tonic water. The holic beverages due to their good alcohol fastness. Further, the dyestuffs of formula I, when dyed on paper, have good nuance stability.

The compounds of formula I are advantageously used in acid addition salt form, e.g. in salt form obtained by the addition of a carboxylic acid such as acetic acid, lactic acid, formic acid or glycolic acid, or quaternary ammonium salt form. The compounds of formula I in which Y is other than hydrogen may be used directly as dyes or may be suitably worked up into solid or stable liquid-aqueous dyeing preparations, according to known methods, advantageously by grinding or granulating or by dissolving in suitable solvents, optionally adding an assistant, e.g. a stabiliser, a solubilising or a diluting agent such as urea. Such preparations may be obtained, for example, as described in French Patent Specifications 1,572,030 and 1,581,900 or in accordance with German DOS 2,001,748 and 2,001,816.

Liquid dyeing compositions are preferably as follows:
1 part by weight of a compound of formula I (in acid addition salt form or quaternary ammonium salt form);
0.01-1 part by weight of an inorganic salt (preferably 0.01 to 0.1 part);
0.01-1 part by weight of an organic acid such as formic, acetic, lactic, citric, propionic or methoxy acetic acid;
1-8 parts by weight of water; and
0-5 parts by weight of a solubilising agent such as a glycol (diethylene glycol, triethylene glycol or hexylene glycol), a glycol ether such as methyl cellosolve, methyl carbitol, butyl polyglycol, urea, formamide and dimethylformamide.

Solid dyeing preparations are preferably as follows:
1 Part by weight of a compound of formula I (in acid addition salt form or quaternary ammonium salt iorm);
0.01-1 part by weight of an inorganic salt (preferably 0.01 to 0.1 part); and
0-8 parts by weight of a standardising agent (preferably non-ionic such as urea, dextrin, glucose or d-glucose).

The solid compositions may usually contain up to 10% residual moisture. In the following Examples, all parts and percentages are by weight; the temperatures are given in degrees celsius.

EXAMPLE 1

(a) 198 Parts (2 moles) of cyanoacetic acid methyl ester are added dropwise at 15°-20° over the course of 2 hours to 258 parts (2 moles) of I-(2'-aminoethyl)piperazine, and the mixture is stirred for 4 hours. Then, 232 parts (2 moles) of acetoacetic acid methyl ester, 45 parts (0.75 mole) of glacial acetic acid and 170 parts (2.5 moles) of a ca. 25% ammonia solution are added, and stirring is effected for 24 hours at 50°-60°. The beige suspension is discharged onto water and the precipitated product of the formula

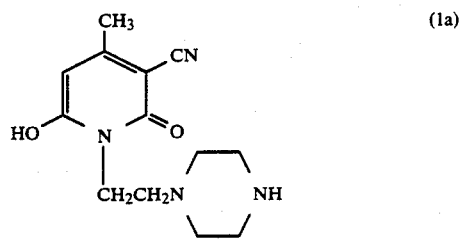

is filtered off.

(b) Compound (1a) is hydrolyzed and decarboxylated in sulphuric acid at 135°-155° by known methods to form the compound of the formula

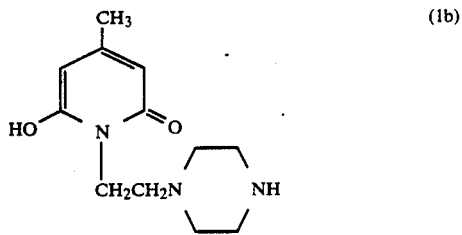

(c) Compounds (1a) and (1b), respectively, are each reacted in water by known methods at about 80°-90° and at a pH of 9 with a compound of the formula

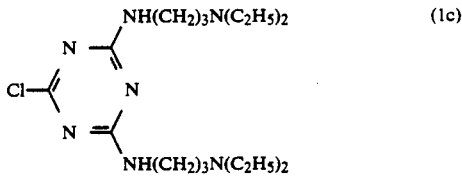

to form the compound of the formula

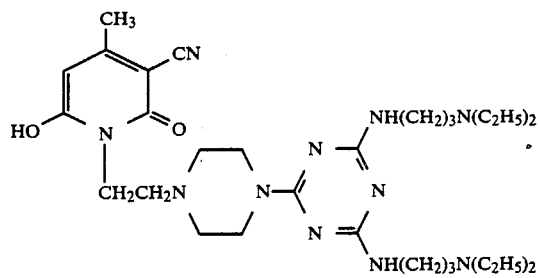

and the compound of the formula

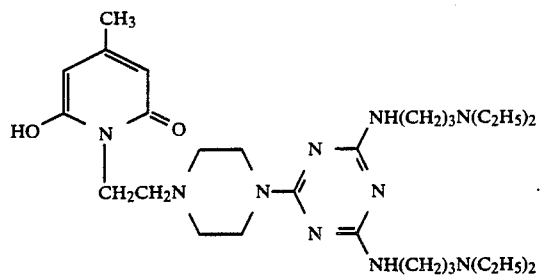

These compounds (1d) and (1e) are well soluble in water, particularly in an acidic medium, and can be used without isolation as coupling components for the production of azo dyes.

EXAMPLE 2

(a) A small excess pyridine is quaternised by known methods with 1 mole of chloroacetic acid methyl ester and reacted in methanol at 20°–25° together with 1 mole of 1-(2'-aminoethyl)piperazine to form the compound of the formula

(b) Without isolating compound (2a), acetoacetic acid methyl ester is added to the reaction mixture, and cyclisation is effected by known methods at about 40°–50°, whilst adding a ca. 50% potassium hydroxide solution to form the pyridone of the formula

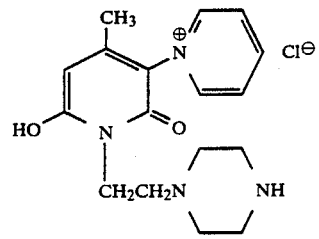

(c) After addition of water, the methanol is distilled off, and the resultant compound (2b) is reacted by known methods at about 80°–90° and at a pH of 9 with the compound (1c) to form the compound of the formula

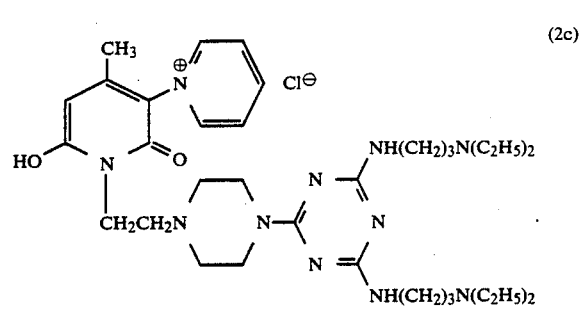

Compound (2c) is well soluble in water, especially in an acidic medium, and can be used without isolating as a coupling component for the production of azo dyes.

EXAMPLE 3

24 Parts (0.1 mole) of 2-(4'-aminophenyl)-6-methylbenzothiazole are stirred into 350 parts water and 30 parts of a ca. 25% hydrochloric acid solution, and are diazotised in conventional manner with 6.9 parts (0.1 mole) of sodium nitrite.

59.7 Parts (0.1 mole) of the compound (1d) dissolved in water are then added dropwise. The pH is maintained at 4–5 by adding sodium bicarbonate. Coupling is complete after one hour, and and the dyestuff of the formula

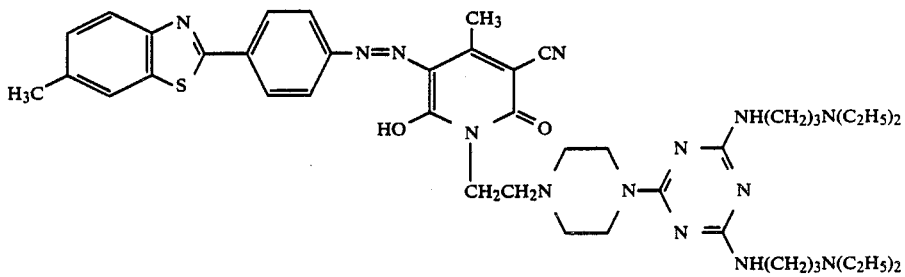

which precipitates at pH 7–8 is filtered off and dissolved in an acidic medium. It dyes paper in orange shades. It may also be used for dyeing cotton, leather or polyacrylonitrile.

EXAMPLE 4

By a method analogous to that of Example 3, but using an aqueous solution of compound (2c) as coupling component, the dyestuff of the formula

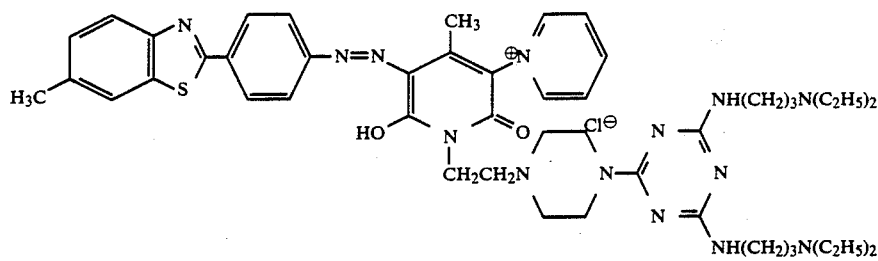

is obtained; it gives brilliant orange dyeings on paper.

EXAMPLE 5

19.8 Parts (0.1 mole) of 4,4'-diaminodiphenylmethane are tetrazotised according to known methods at 0°–5° in 200 parts water and 60 parts of a 30% hydrochloric acid solution, with 13.8 parts (0.2 mole) of sodium nitrite. 0.2 Mole of the compound (2c), dissolved in water, is added dropwise to the ice-cold tetrazo solution over the course of 30 minutes. The pH is adjusted to 4.5–5.0 by adding a 30% sodium hydroxide solution. The resultant dyestuff of the formula

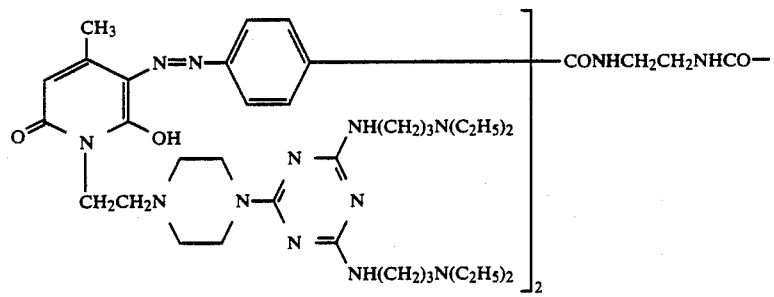

which is in solution, can be used directly for dyeing paper a yellow shade.

EXAMPLE 6

By a method analogous to that of Example 5, but using 29.8 parts (0.1 mole) of N,N-bis(p-aminobenzoyl)ethylenediamine instead of 19.8 parts of 4,4'-diaminodiphenylmethane, and 0.2 mole of compound (1e) instead of compound (2c), respectively, a dyestuff of the formula

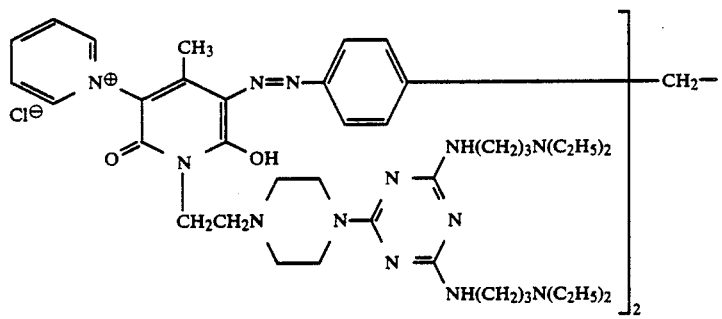

is obtained which precipitates when adjusting the pH at 9.5–10 by adding a 30% sodium hydroxide solution. This dyestuff, in acid addition salt form, preferably as acetate, dyes paper a brilliant yellow shade. The paper dyeing have perfect back-water and wet fastness properties.

EXAMPLES 7 TO 32 /TABLE

By a method analogous to that described in Example 5 or 6, further compounds of formula I may be prepared using appropriate starting compounds. They correspond to formula (A)

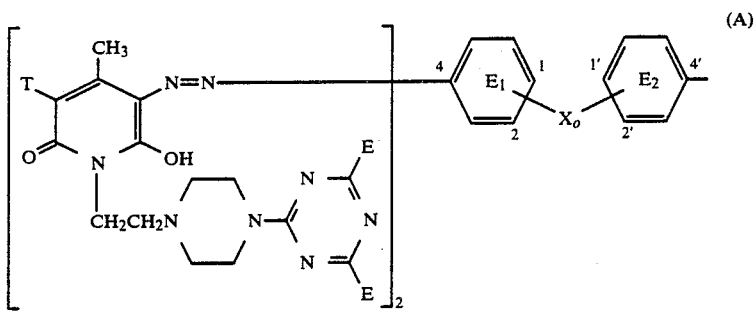
(A)

in which the symbols are as defined in the Table below. In the Table, T has the following significanes:

T₁ is H
T₂ is —CN
T₃ is

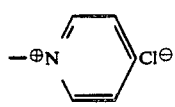

T₄ is

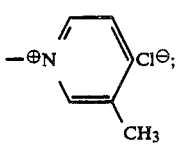

and E has the following significances:
E₁ is —NH(CH₂)₂N(C₂H₅)₂
E₂ is —NH(CH₂)₃N(C₂H₅)₂
E₃ is

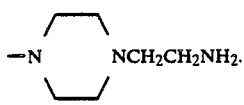

In the last column of the Table the shade of the dyeing on paper is given whereby
 is a yellow and b is orange.

The paper dyeings obtained with the dyestuffs of Examples 7 to 32 in conventional manner have good light fastness and wet fasteness properties. The backwater is practically colourless.

TABLE

| Ex. No. | T | E | X₀ | position of X₀ on ring E₁ and ring E₂ | shade on paper |
|---|---|---|---|---|---|
| 7 | T₃ | E₁ | —CH₂— | 1,1' | a |
| 8 | T₄ | E₁ | " | " | a |
| 9 | T₃ | E₃ | " | " | a |
| 10 | T₄ | E₂ | " | " | a |
| 11 | T₁ | E₂ | " | " | a |
| 12 | T₂ | E₂ | " | " | a |
| 13 | T₁ | E₃ | " | " | a |
| 14 | T₁ | E₁ | —CH₂CH₂— | " | a |
| 15 | T₂ | E₁ | " | " | a |
| 16 | T₂ | E₂ | " | " | a |
| 17 | T₃ | E₂ | " | " | a |
| 18 | T₁ | E₂ | —CONH— | " | b |

TABLE-continued

| Ex. No. | T | E | X₀ | position of X₀ on ring E₁ and ring E₂ | shade on paper |
|---|---|---|---|---|---|
| 19 | T₂ | E₂ | " | " | b |
| 20 | T₃ | E₂ | " | " | b |
| 21 | T₁ | E₂ | " | 1,2' | a |
| 22 | T₂ | E₂ | " | " | a |
| 23 | T₃ | E₂ | " | " | a |
| 24 | T₃ | E₂ | —CONHCH₂CH₂NHCO— | 1,1' | a |
| 25 | T₁ | E₁ | —CONHCHCH₂NHCO—  \| CH₃ | " | a |
| 26 | T₁ | E₂ | " | " | a |
| 27 | T₂ | E₂ | " | " | a |
| 28 | T₁ | E₂ | —CON(piperazine)NCO— | " | a |
| 29 | T₁ | E₂ | —CONHCH₂CH₂OC(O)— | " | a |
| 30 | T₁ | E₂ | —CONCH₂CH₂NCO— \| CH₃ \| CH₃ | " | a |
| 31 | T₁ | E₂ | —SO₂NHCH₂CH₂NHSO₂— | " | a |
| 32 | T₁ | E₂ | —SO₂—N(piperazine)N—SO₂— | " | a |

In the following examples, the application of the compounds of this invention is illustrated.

Application Example A

70 Parts of chemically bleached sulphite cellulose obtained from pinewood and 30 parts of chemically bleached sulphite cellulose obtained from birchwood are ground In 2000 parts of water In a hollander. 0.2 Parts of the dyestuff of Example 3 or 6 (each used in acid addition salt form) are sprinkled into this pulp. Paper is produced from this pulp after mixing for 20 minutes. The absorbent paper which is obtained in this manner is dyed In an orange (brillian yellow) tone. The waste water is colourless.

Application Example B 0.5 Parts of the dyestuff solution of Example 3 or 6 (each used in acid addition salt form) are added to 100 parts of chemically bleached sulphite cellulose which have been ground in a hollander with 2000 parts of water. Sizing takes place after a thorough mixing for 15 minutes. The paper which is produced from this material has an orange (brilliant yellow) tone and has excellent wet fastness properties.

Application Example C

An absorbent length of unsized paper Is drawn at a temperature of 40°-50° through a dyestuff solution having the following composition:
0.5 parts of the dyestuff of Example 3 or 6 (each in acid addition salt form),
0.5 parts of starch, and
99.0 parts of water.

The excess dyestuff solution Is squeezed out through two rollers. The dzled lenSth of paper is dyed in an orange (brilliant yellow) tone and has good fastness properties.

Any one of the dyestuffs of Examples 4, 5 and 7 to 32 may also be used either in its water-soluble salt form or in form of a dyeing preparation, e.g. granules, in any one of Applicayion Examples A to C.

Application Example D

100 Parts of freshly tanned and neutralised chrome leather are agitated for 30 minutes in a vessel with a bath of 250 parts of water at 55° and 1 part of the dyestuff of Example 3 or 6 (in acid addition salt form). and are then treated in the same bath for a further 30 minutes with 2 parts of an anionic fatty liquor based on sulphonated train oil. The leather is then dried and prepared in the normal way, giving a leather evenly dyed in an orange (yellow) tone.

Further low-affinity, vegetable-tanned leathers can similarly be dyed by known methods. Dyeing can also take place analogously using the dyes of the remaining examples.

Application Example E

2 Parts of the dyestuff of Example 3 or 6 (in acid addition salt form) are dissolved in 4000 parts of demineralised water and heated to 40°. 100 Parts of a pre-wetted cotton tabric are added and the bath is heated to boiling temperature within 30 minutes and held at the boil for one hour, topping up with water where necessary. After removing the dyed fabric from the bath, rinsing with water and drying, an orange (yellow) cotton dyeing is obtained having good light fastness and wet fastness properties. The dyestuff exhausts practlcally quantitatively onto the fibre, and the waste water is practically colourless.

Any one of the dyestuffs of Examples 4, 5 and 7 to 32 may be used in place of that of xample 3 or 6 in any one of Application Examples D and E.

Application Example F 15 kg of waste paper, 25 kg of bleached mechanical wood pulp and 10 kg unbleached sulphate cellulose are defibrated in a pulper to a 3% aqueous pulp slurry. This stock suspension is diluted to 2% in a dyeing chest. To this diluted suspension there are added 5% by weigh: kaolin and then 1.25 kg of a 5% acetic acid solution of the dyestuff of Example 6, the % being based on the dry weight of fibres, whilst stirring. After 20 minutes, a 1% rosin size dispersion (based on the weight of absolutely dry fibres) is added to the resulting pulp in the mixing chest. The homogeneous pulp slurry is then adjusted to pH 5 by the addition of alum in the paper machine shortly before starting up.

A 80g/m² yellow mill-finished bag paper is produced on the paper machine. The resulting dyed paper exhibits very good fastness to bleeding according to DIN 53 991 and good light iastness properties.

The resulting paper can be almost completely decolourized with hypochlorite.

Application Example G

A dry pulp consisting of 60% mechanical wood pulp and 40% unbleached sulphite cellulose is beaten in a hollander with sufficient water and up to a grinding rate of 40 SR, for the dry content to be just above Z.5%, and is then adjusted with water to exactly 2.5% dry content of the thick pulp. 200 Parts of this thick pulp are mixed with 5 parts of a 0.25% aqueous solution of the dye of Example 6 and stirred for ca. 5 minutes es. Then Z% rosin size and 4% alum based on the dry weiht are added and again homogeneous stirring is effected for a further few minutes. The mass is diluted with ca. 500 parts of water to 700 parts by volume, and paper sheets are formed in known manner by drawing through a sheet former. They have an intense brillianI yellow colour. In the waste water of the sheet former, the quantity of dye that is not fixed to the paper is measured photometrically at ca. 3%. When dyeing unsized paper pulp, ca. 4% of unfixed dye is found, with the process otherwise the same.

Any one of the dyestuffs of Examples 3 to 5 and 7 to 3Z may be used in place of that of Example 6 in any one of Application Examples F and G. The waste water exhibits a substantially low residual dyestuff concentration.

What is claimed is:

1. A metal-free compound of the formula $$\begin{array}{c} R \\ T \diagup \diagdown Y \\ \| \quad \| \\ O \diagdown N \diagup OH \\ | \\ A_1-B_1-Z \end{array}$$

a 1:1 or 1:2 metal complex of a metallizable compound of said formula or an acid addition salt of a metal-free compound of said formula or of a 1:1 or 1:2 metal complex thereof, wherein $A_1$ is linear or branched $C_{1-8}$alkylene; linear or branched $C_{2-8}$alkylene substituted by 1 or 2 substituents selected from hydroxy, halo and cyano; linear or branched $C_{2-8}$alkenylene; cyclohexylene; cyclohexylene substituted by 1 to 3 $C_{1-4}$alkyl gruops; phenylene or phenylene substituted by 1 or 2 substituents selected from halo, $C_{1-4}$alkyl and $C_{1-4}$alkoxy, $B_1$ is $$-N\diagup\diagdown N- \quad \text{or} \quad -\overset{\oplus}{\underset{R_4}{N}}\diagup\diagdown N- \quad A^{\ominus},$$

wherein the quaternized nitrogen atom is bound to a carbon atom of $A_1$,

R is hydrogen, $C_{1-4}$alkyl, $C_{5-6}$cycloalkyl, phenyl, benzyl or phenylethyl, T is hydrogen, cyano, —COOR$_1$, —CON(R$_2$)$_2$, —SO$_2$N(R$_2$)$_2$,

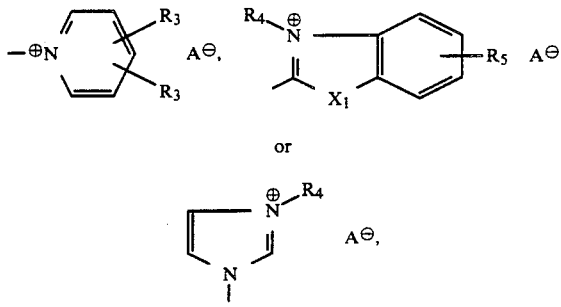

or where
R$_1$ is $C_{1-6}$alkyl or phenyl($C_{1-3}$alkyl),
each R$_3$ is independently hydrogne, $C_{1-4}$-alkyl, —CON(R$_2$)$_2$or —N(R$_5$)$_2$, and
X$_1$ is —S—, —O— or —NR$_5$—,
Y is —N=N—D or —X—F,
wherein
D is the radical of a diazo component,
F is a chromophoric grup, and
X is a divalent radical,
Z is

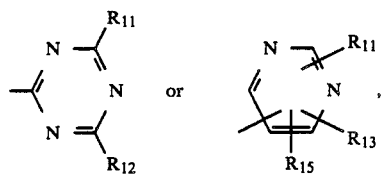

wherein
R$_{11}$ is —NR$_5$—A$_2$—W,

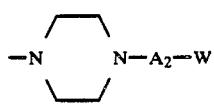

or —NR$_5$—A$_2$—NR$_5$—A$_2$—W,
wherein
W is —NR$_6$R$_7$ or —⊕NR$_8$R$_9$R$_{10}$ A$\beta$,
R$_{12}$ is —NR—A$_2$—W,

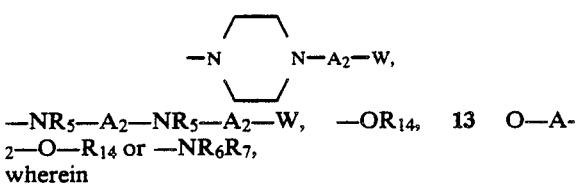

—NR$_5$—A$_2$—NR$_5$—A$_2$—W, —OR$_{14}$, 13 O—A$_2$—O—R$_{14}$ or —NR$_6$R$_7$,
wherein
W is as defined above,
R$_{13}$ is hydrogen, halo, $C_{1-4}$alkyl, —O—R$_{14}$, —O—A$_2$—O—R$_{14}$ or —NR$_6$R$_7$, and
R$_{15}$ is hydrogen or halo,
wherein
each A$_1$ is independently linear or branched $C_{2-8}$alkylene or linear or branched $C_{3-8}$alkylene mono-substituted by hydroxy, each R$_2$ is independently hydrogen or $C_{1-4}$alkyl, or
—N(R$_2$)$_2$ is a saturated ring containing, in addition to the depicted nitrogen atom, 0 to 2 radicals selected from —O—, —S—, and —NH—, which ring is unsubstituted or substituted by 1 to 3 $C_{1-4}$alkyl groups,
each R$_4$ is independently $C_{1-4}$alkyl,
each R$_5$ is indepencently hydrogen or $C_{1-4}$alkyl,
each R$_6$ is independently hydrogen; $C_{1-4}$alkyl; $C_{2-4}$alkyl monosubstituted by hydroxy or $C_{1-4}$alkoxy; cyclohexyl or phenyl($C_{1-4}$alkyl),
each R$_7$ is indepenently hydrogen; $C_{1-4}$alkyl; $C_{2-4}$alkyl monosubstituted by hydroxy or $C_{1-4}$alkoxy; cyclohexyl; phenyl or phenyl($C_{1-4}$alkyl), or
—NR$_6$R$_7$ is a saturated ring containing, in addition to the depicted nitrogen atom, 0 to 2 radicals selected from —O—, —S— and —NH—, which ring is unsubstituted or substituted by 1 to 3 $C_{1-4}$alkyl gorups or is N'-amino($C_{2-3}$alkyl)-piperazino,
each R$_8$ and R$_9$ is independently $C_{1-4}$alkyl or $C_{2-4}$-alkyl monosubstituted by hydroxy or $C_{1-4}$alkoxy, and R$_{10}$ is $C_{1-4}$alkyl or phenyl($C_{1-4}$alkyl), or
—⊖NR$_8$R$_9$R$_{10}$ is pyridinium; pyridinium substituted by 1 to 3 $C_{1-4}$alkyl groups; a saturated ring containing, in addition to the depicted nitrogen atom, 1 to 3 radicals selected from —O—, —S— and —NH—, which ring is unsubstituted or substituted by 1 to 3 $C_{1-4}$alkyl groups; or N—$C_{1-4}$alkyl—N'-amino($C_{2-3}$alkyl)piperazinium,
each R$_{14}$ is independently hydrogen, $C_{1-4}$alkyl or phenyl, and
each A⊖ is independently a non-chromophoric anion, wherein each halo is independently fluoro, chloro or bromo, with the provisos that (i) each metal-free compound, 1:1 and 1:2 metal complex and acid addition salt is free of sulfo groups, and (ii) the hydroxy groups of each alkylene radical substituted by two hydroxy groups are attached to different carbon atoms.

2. A metal-free compound, 1:1 or 1:2 metal complex or acid addition salt according to claim 1, wherein
each R$_2$ is independently hydrogen or $C_{1-4}$alkyl, or
—N(R$_2$)$_2$ is piperidino, morpholino, piperazino or N'-$C_{1-4}$alkylpiperazino,
each R$_6$ is independently hydrogen; $C_{1-4}$alkyl; $C_{2-4}$alkyl monosubstituted by hydroxy or $C_{1-4}$alkoxy; cyclohexyl or phenyl($C_{1-4}$alkyl),
each R$_7$ is independently hydrogen; $C_{1-4}$alkyl; $C_{2-4}$alkyl monosubstituted by hydroxy or $C_{1-4}$alkoxy; cyclohexyl; phenyl or phenyl($C_{1-4}$alkyl), or
—NR$_6$R$_7$ is piperidino, morpholino, pieprazino, N'-$C_{1-4}$alkylpiperazino or N'-(amino-(CH$_2$)$_r$-)piperazino,
each R$_8$ and R$_9$ is independently $C_{1-4}$alkyl or $C_{2-4}$alkyl monosubstituted by hydroxy or $C_{1-4}$alkoxy, and R$_{10}$ is $C_{1-4}$alkyl or phenyl($C_{1-4}$alkyl), or
—⊕NR$_8$R$_9$R$_{10}$ is pyridinium, pyridinium substituted by 1 to 3 $C_{1-4}$alkyl groups or

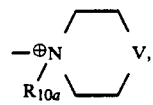

wherein
$R_{10a}$ is methyl, ethyl or benzyl, and V is a direct bond, —CH$_2$—, —O—, —NH—, —N(C$_{1-4}$alkyl)—,

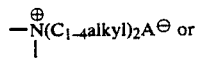

or

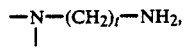

wherein each t is independentloy 2 or 3.

3. A metal-free compound, 1:1 or 1:2 metal complex or acid addition salt according to claim 1 wherein R is methyl, ethyl or phenyl.

4. A metal-free compound, 1:1 or 1:2 metal complex or acid addition salt according to claim 1 wherein T is hydrogen, cyano or

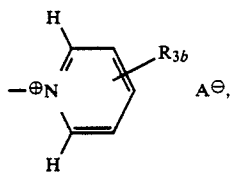

wherein $R_{3b}$ is hydrogen or methyl.

5. A metal-free compound, 1:1 or 1:2 metal complex or acid addition salt according to claim 4 wherein T is hydrogen.

6. A metal-free compound, 1:1 or 1:2 metal complex or acid addition salt according to claim 2 wherein B$_1$ is

7. A metal-free compound, 1:1 or 1:2 metal complex or acid addition salt according to claim 6 wherein A$_1$ is linear or branched C$_{2-3}$alkylene, linear or branched C$_{3-4}$alkylene monosubstituted by hydroxy, 1,4-cyclohexylene, 1,3-phenylene or 1,4-phenylene.

8. A metal-free compound, 1:1 or 1:2 metal complex or acid addition salt according to claim 6 wherein Z is

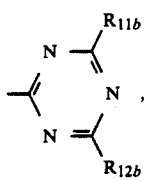

wherein
$R_{11b}$ is —NR$_{5a}$—A$_{2b}$—W$_b$, and
$R_{12b}$ is —NR$_{5a}$—A$_{2b}$—W$_b$, —O—R$_{14b}$, —O—A$_{2b}$—O—R$_{14b}$ or —NR$_{6b}$R$_{7b}$,
wherein
$R_{14b}$ is hydrogen, methyl or ethyl,
wherein
each A$_{2b}$ is independently linaer C$_{2-3}$alkylene,
each R$_{5a}$ is independently hydrogen, methyl or ethyl, and each W$_b$ is independently —NR$_{6b}$R$_{7b}$ or —⊕NR$_{8b}$R$_{9b}$R$_{10b}$ A⊖, wherein
each R$_{6b}$ and R$_{7b}$ is independently hydrogen, methyl or ethyl,
each R$_{8b}$ and R$_{9b}$ is methyl or ethyl, and
$R_{10b}$ is is methyl, ethyl or benzyl.

9. A metal-free compound, 1:1 or 1:2 metal complex or acid addition salt according to claim 1 wherein
Y is —N=N—F$_b$,
wherein
F$_b$ is

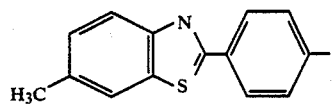

or the ardical of a monoazo, disazo or polyazo dye.

10. A metal-free compound according to claim 1 or an acid addition salt thereof.

11. A metal-free compound according to claim 1 having the formula

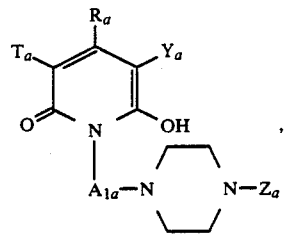

a 1:1 or 1:2 metal complex of a metallizable compound of said formula or an acid addition salt of a metal-free compound of said formula or of a 1:1 or 1:2 metal complex thereof, wherein
A$_{1a}$ is linear or branched C$_{1-6}$alkylene; linear or branched C$_{2-3}$alkylene monosubstituted by hydroxy; 1,4-cyclohexylene; 1,3-phenylene; 1,4-phenylene; or 1,3-phenylene or 1,4-phenylene monosubstituted by chloro, methyl or methoxy,
$R_a$ is methyl, ethyl, cyclohexyl, phenyl or benzyl,
$T_a$ is hydrogen, cyano, —COOR$_{1b}$, —CON(R$_{2a}$)$_2$ or

wherein
$R_{1b}$ is methyl, ethyl or benzyl,
each R$_{2a}$ is independently hydrogen, methyl or ethyl, or
—N(R$_{2a}$)$_2$ is piperidino, morpholino, piperazino or N'-(C$_{1-4}$alkyl)piperazino, and
each R$_{3a}$ is independently hydrogen, methyl, ethyl, —CON(R$_{2b}$)$_2$ or —N(R$_{5a}$)$_2$,
wherein
each R$_{2b}$ is independently hydrogen, methyl or ethyl,
$Y_a$ is —N=N—F$_b$,
wherein
F$_b$ is

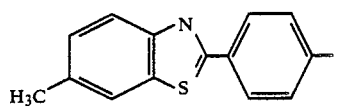

or the radical of a monoazo, disazo or polyazo dye, and $Z_a$ is

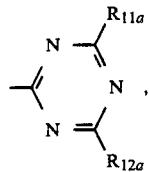

wherien $R_{11a}$ is $—NR_{5a}—A_{2a}—W_a$,

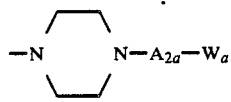

or $—NR_{5a}—A_{2a}—NR_{5a}—A_{2a}—W_a$, and
$R_{12a}$ is $—NR_{5a}—A_{2a}—W_a$,

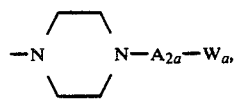

$—NR_{5a}—A_{2a}'NR_{5a}—A_{2a}—W_a$, $—O—R_{14a}$,
$—O—A_{2b}—O—R_{14a}$ or $—NR_{6a}R_{7a}$,
wherein
  $A_{2b}$ is linear $C_{2-3}$alkylene, and
  $R_{14a}$ is hydrogen, methyl, ethyl or phenyl,
wherein
  each $A_{2a}$ is independently linear or branched $C_{2-4}$alkylene or linear or branched $C_{3-4}$alkylene monosubstituted by hydroxy,
  each $R_{5a}$ is independently hydrogen, methyl or ethyl, and
  each $W_a$ is independently $—NR_{6a}R_{7a}$ or $—⊕NR_{8a}R_{9a}R_{10a}$ $A^⊖$,
wherein
  each $R_{6a}$ is independently hydrogen; methyl; methyl; $C_{2-3}$alkyl monosubstituted by hydoxy or methoxy; cyclohexyl or phenyl($C_{1-2}$alkyl),
  each $r_{7a}$ is independently hydrogen; methyl; ethyl; $C_{2-3}$alkyl monosubstituted by hydroxy or methoxy; cyclohexyl; phenyl or phenyl($C_{1-2}$alkyl), or
  $—NR_{6a}R_{7a}$ is piperidino, morpholino, piperazino, N'-($C_{1-4}$-alkyl)piperazino or N'-(amino—$(CH_2)_t$-)piperazino, wherein t is 2 or 3,
  each $R_{8a}$ and $R_{9a}$ is independently methyl or ethyl, and
  $R_{10a}$ is methyl, ethyl or benzyl, or
  $—⊕NR_{8a}R_{9a}R_{10a}$ is pyridnium, picolinium, lutidinium or

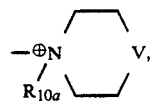

wherein
V is a direct bond, $—CH_2—$, $—O—$, $—NH—$,
$—(C_{1-4}alkyl)—$,

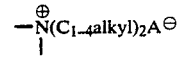

or
$—N((Ch_2)_t—NH_2)—$,
wherein
  t is 2 or 3, and
  $R_{10a}$ is as defined above.

12. A metal-free compound, 1:1 or 1:2 metal complex or acid addition salt according to cliam 11 wherein $R_a$ is methyl.

13. A metal-free compound, 1:1 or 1:2 metal complex or acid addition salt according to claim 12 wherien
  $A_{1a}$ is linear or branched $C_{2-3}$alkylene, and
  $Z_a$ is

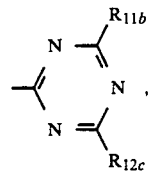

wherein
each of $R_{11b}$ and $R_{12c}$ is independently $—NR_{5a}—A_{2b}—W_b$,
wherein
  $A_{2b}$ is linear $C_{2-3}$alkylene, and
  $W_b$ is $—NR_{6b}R_{7b}$ or $—⊕NR_{8b}R_{9b}R_{10b}$ $A^⊖$,
wherein
  each $R_{6b}$ and $R_{7b}$ is independently hydrogen, methyl or ethyl,
  each $R_{8b}$ and $R_{9b}$ is methyl or ethyl, and
  $R_{10b}$ is methyl, ethyl or benzyl.

14. A metal-free compound, 1:1 or 1:2 metal complex or acid addition salt according ot claim 11 wherein $T_a$ is hydrogen, cyano or

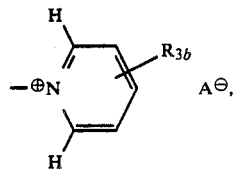

wherien $R_{3b}$ is hydrogen or methyl.

15. A metal-free compound, according to claim 11 or an acid addition salt thereof.

16. A metal-free compound according to claim 11 having the formula

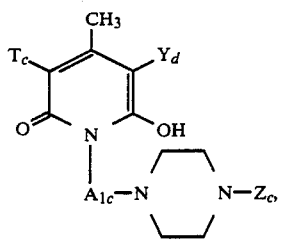

or an acid addition salt thereof,
wherein
$Y_d$ is —N=N—$F_e$,
wherein
$F_e$ is

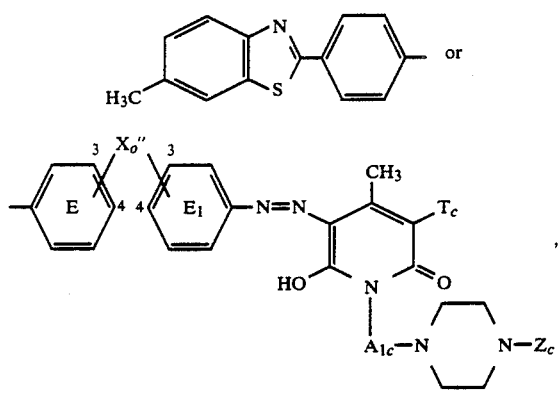

wherein
$X_o''$ is —(CH$_2$)$_p$—, —CONH— or —CO—NR$_{3b}$—A$_{2-}$
$_b$—NR$_{3b}$—CO—, wherein p is 1 or 2, with the
proviso that $X_o''$ is attached to the 3- or 4-position
of Ring E and the 3-or 4-position of Ring E$_1$,
wherein
each A$_{1c}$ is independently linear or branched C$_{2-}$
$_3$alkylene, each T$_c$ is independently hydrogen,
cyano or

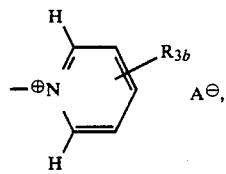

and
each Z$_c$ is independently

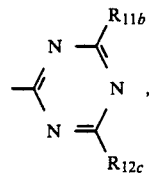

wherien
each of R$_{11b}$ and r$_{12c}$ is independently —NR$_{5a}$—A$_{2-}$
$_b$—W$_b$,
wherein
W$_b$ is —NR$_{6b}$R$_{7b}$ or —⊕NR$_{8b}$R$_{9b}$R$_{10b}$ A⊖
wherein
each A$_{2b}$ is independently linear C$_{2-3}$alkylene,
each R$_{3b}$ is independently hydrogen, methyl or ethyl,
each R$_{8b}$ and r$_{9b}$ is methyl or ethyl, and
R$_{10b}$ is methyl, ethyl or benzyl.

17. A metal-free compound or acid addition salt according to claim 16 wherein each Z$_c$ is

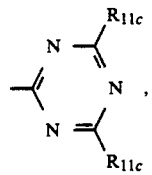

wherein each R$_{11c}$ is —NH—A$_{2b}$—N(C$_2$H$_5$)$_2$, the R$_{11c}$'s being identical.

18. A metal-free compound or acid addition salt according to claim 16 wherein each T$_c$ is hydrogen.

19. The metal-free compound according to claim 18 having the formula

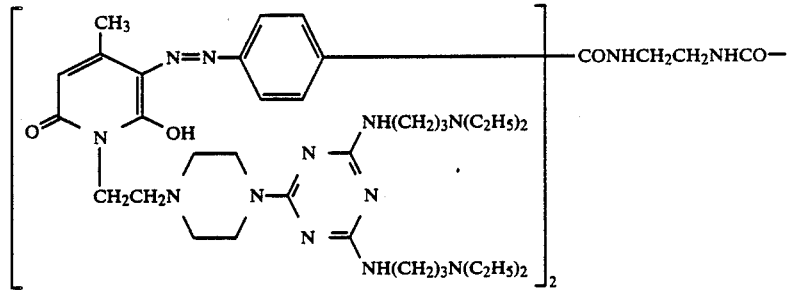

or an acid addition salt thereof.

20. The metal-free compound according to claim 19 in acetic acid addition salt form.

21. The metal-free compound according to claim 18 having the formula

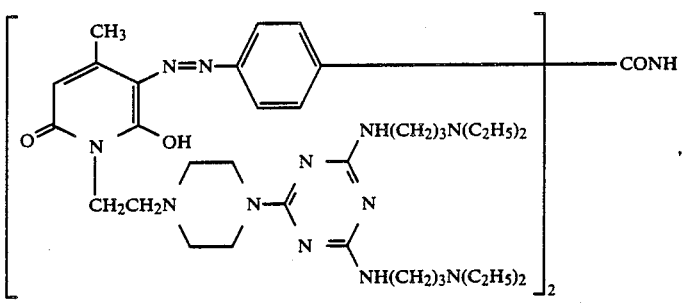

or an acid addition salt thereof.

22. The metal-free compound according to claim 11 having the formula

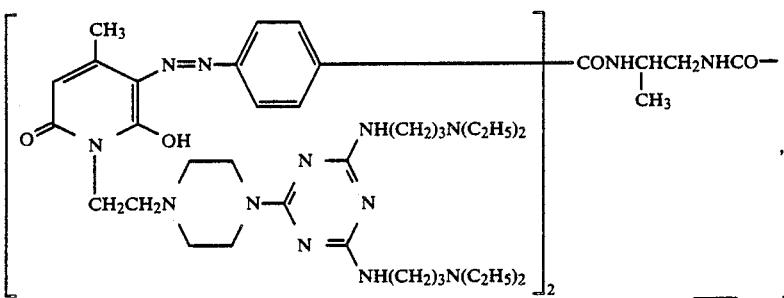

or an acid addition salt thereof.

23. A compound of the formula

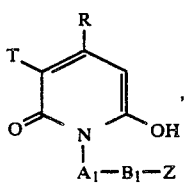

or an acid addition sal thereof,
wherien
$A_1$ is linear or branched $C_{1-8}$alkylene; linear or branched $C_{2-8}$alkylene substituted by 1 or 2 substituents selected from hydroxy, halo and cyano; linear or branched $C_{2-8}$alkenylene; cyclohexylene; cyclohexylene substituted by 1 to 3 $C_{1-4}$alkyl gruops; phenylene or phenylene substituted by 1 or 2 substituents selected from halo, $C_{1-4}$alkyl and $C_{1-4}$alkoxy,
$B_1$ is

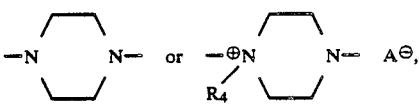

wherein the quaternized nitrogen atom is bound to a carbon atom of $A_1$,
R is hydrogen, $C_{1-4}$alkyl, $C_{5-6}$cycloalkyl, phenyl, benzyl or phenylethyl,
T is hydrogen, cyano, $-COOR_1$, $-CON(R_2)_2$, or $-SO_2N(R_2)_2$,

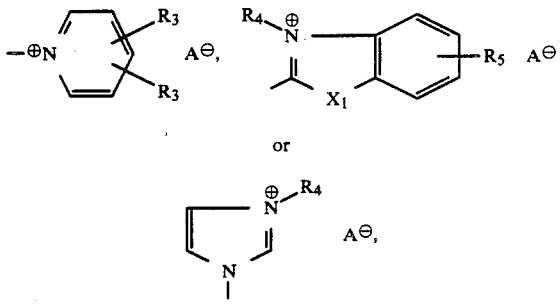

wherein
$R_1$ is $C_{1-6}$alkyl or phenyl ($C_{1-3}$alkyl),
each $R_3$ is independently hydrogen, $C_{1-4}$-alkyl, $-CON(R_2)_2$ or $-N(R_5)_2$, and
$X_1$ is $-S-$, $-O-$ or $-NR_5-$, and
Z is

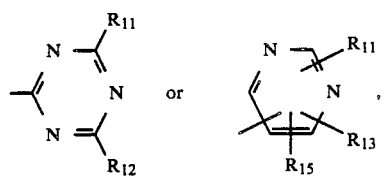

wherein
$R_{11}$ is

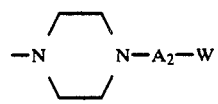

or
wherein

W is —NR$_6$R$_7$ or —⊕NR$_8$R$_9$R$_{10}$ A⊖,
R$_{12}$ is

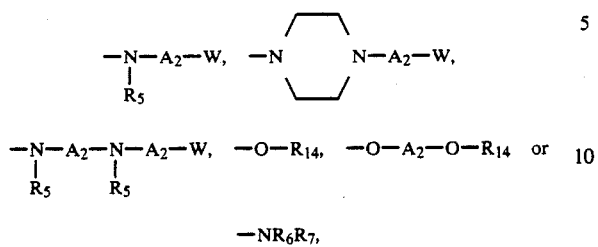

wherein
W is as defined above,
R$_{13}$ is hydrogen, halo, C$_{1-4}$alkyl, —O—R$_{14}$, —O—A$_2$—O—R$_{14}$ or —NR$_6$R$_7$, and
R$_{15}$ is hydrogen or halo,
wherein
each A$_2$ is independently linear or branched C$_{2-8}$alkylene or linear or branched C$_{3-8}$alkylene monosubstituted by hydroxy,
each R$_2$ is independently hydrogen or C$_{1-4}$alkyl, or —N(R$_2$)$_2$ is a saturated ring containing, in addition to the depicted nitrogen atom, 0 to 2 radicals selected from —O—, —S— and —NH—, which ring is unsubstituted or substituted by 1 to 3 C$_{1-4}$alkyl groups,
each R$_4$ is independently C$_{1-4}$alkyl,
each R$_5$ is independently hydrogen or C$_{1-4}$alkyl,
each R$_6$ is independently hydrogen; C$_{1-4}$alkyl; C$_{2-4}$alkyl monosubstituted by hydroxy or C$_{1-4}$alkoxy; cyclohexyl or phenyl(C$_{1-4}$alkyl),
Each R$_7$ is independently hydrogen; C$_{1-4}$alkyl; C$_{2-4}$alkyl monosubstituted by hydroxy or C$_{1-4}$alkoxy; cyclohexyl; phenyl or phenyl (C$_{1-4}$alkyl), or
—NR$_6$R$_7$ is a saturated ring containing, in addition to the depicted nitrogen atom, 0 to 2 radicals selected from —O—, —S— and —NH—, which ring is unsubstituted or substituted by 1 to 3 C$_{1-4}$alkyl groups or is N'-amino(C$_{2-3}$-alkyl)piperazino,
each R$_8$ and R$_9$ is independelty C$_{1-4}$alkyl or C$_{2-4}$-alkyl monosubustituted by hydroxy or C$_{1-4}$alkoxy, and
R$_{10}$ is C$_{1-4}$alkyl or phenyl (C$_{1-4}$alkyl), or —⊕NR$_8$R$_9$R$_{10}$ is pyridinium; pyridinium substituted by 1 to 3 C$_{1-4}$alkyl grups; a saturated ring containing, in addition to the depicted nitrogen atom, 0 to 2 radicals selected from —O—, —S— and —NH—, which ring is unsubstituted or substituted by 1 to 3 alkyl grups; or N—C$_{1-4}$-alkyl—N'-amino(C$_{2-3}$alkyl)piperazinium,
each R$_{14}$ is independently hydrogen, C$_{1-4}$alkyl or phenyl, and
each A⊖ is independently a non-chromophoric anion, wherein each halo is independently fluoro, chloro or bromo, with the proviso that the hydroxy group of each alkylene radical substituted by two hydroxy groups are attached to different carbon atoms.

24. A compound of acid addition salt according to claim 23
wherein
each R$_2$ is independently hydrogen or C$_{1-4}$alkyl, or —N(R$_2$)$_2$ is piperidino, morpholino, piperazino or N'—C$_{1-4}$alkylpiperazino, each R$_6$ is independently hydrogen; C$_{1-4}$alkyl; C$_{2-4}$alkyl monosubstituted by hydroxy or C$_{1-4}$alkoxy; cyclohexyl or phenyl(C$_{1-4}$alkyl),
each R$_7$ is independently h ydrogen; C$_{1-4}$alkyl; C$_{2-4}$alkyl monosubstituted by hydroxy or C$_{1-4}$alkoxy; cyclohexyl; phenyl or phenyl(C$_{1-4}$alkyl), or —NR$_6$R$_7$ is piperidino, morpholino, piperazino, N'-C$_{1-4}$alkylpiperazino or N'-(amino-(CH$_2$)$_r$-piperazino,
each R$_8$ and R$_9$ is independently C$_{1-4}$alkyl or C$_{2-4}$alkyl monosubstituted by hydroxy or C$_{1-4}$alkoxy and R$_{10}$ is C$_{1-4}$alkyl or phenyl(C$_{1-4}$alkyl), or —⊕NR$_8$R$_9$R$_{10}$ is pyrdinium, pyridinium substituted by 1 to 3 C$_{1-4}$alkyl groups or

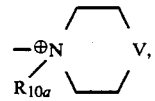

wherein
R$_{10a}$ is methyl, ethyl or benzyl, and V is a direct bond, —CH$_2$—, —O—, —NH—, —N(C$_{1-4}$alkyl)—,

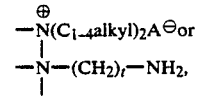

wherein each t is independently 2 or 3.
25. A compound or acid addition salt according to claim 23 wherein R is methyl, ethyl or phenyl.
26. A compound or acid addition salt 23 wherein T is hydrogen, cyano or

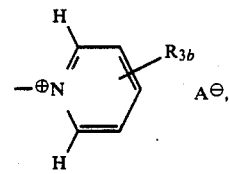

wherein R$_{3b}$ is hydrogen or methyl.
27. A compound or acid addition salt according to claim 26 wherein T is hydrogen.
28. A compound according to calim 23 having the formula

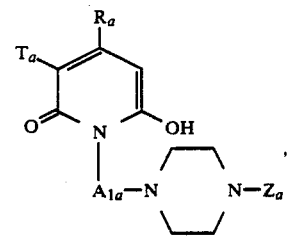

or an acid addition salt thereof,
wherein
A$_{1a}$ is linear or branched C$_{1-6}$alkylene; linear or branched C$_{3-6}$alkylene monosubstituted by hydroxy; 1,4-cyclohexylene; 1,3-phenylene; 1,4-phenylene; or 1,3-phenylene or 1,4-phenylene monosubstituted by chloro, methyl or methoxy,
R$_a$ is methyl, ethyl, cyclohexyl, phenyl or benzyl, $T_a$ is hydrogen, cyano, —COOR$_{1b}$, —CON(R$_{2a}$)$_2$ or

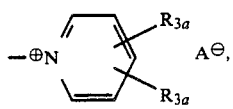

wherein
R$_{1b}$ is methyl, ethyl or benzyl,
each R$_{2a}$ is independently hydrogen, methyl or ethyl or
—N(R$_{2a}$)$_2$ is piperidino, morpholino, piperazino or N'-(C$_{1-4}$alkyl)piperazino, and
each R$_{3a}$ i independently hydrogen, methyl, ethyl, —CON(r$_{2b}$)$_2$ or —N(R$_{5a}$)$_2$,
wherein
each R$_{2b}$ is independently hydrogen, methyl or ethyl, and
Z$_a$ is

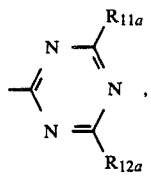

wherein
R$_{11a}$ is —NR$_{5a}$—A$_{2a}$—W$_a$,

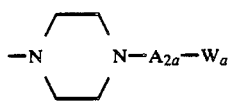

or —NR$_{5a}$—A$_{2a}$—NR$_{5a}$—A$_{2a}$—W$_a$, and
R$_{12a}$ is —NR$_{5a}$—A$_{2a}$—W$_a$,

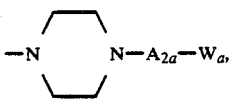

—O—Rhd 14a, —O—A$_b$—O—R$_{14a}$ or —NR$_{6a}$R$_{7a}$,
wherein
A$_{2b}$ is linear C$_{2-3}$alkylene, and R$_{14a}$ is hydrogen, methyl, ethyl or phenyl,
wherein
each A$_{2a}$ is independently linear or branched C$_{2-4}$alkylene or linear or branched C$_{3-4}$alkylene monosubstituted by hydroxy,
each R$_{5a}$ is independently hydrogen, methyl or ethyl, and
each W$_a$ is independently —NR$_{6a}$R$_{7a}$ or —NR$_{8a}$R$_{9a}$R$_{10a}$ A$^\ominus$,
wherein
each R$_{6a}$ is independently hydrogen; methyl; ethyl; C$_{2-3}$alkyl monosubstituted by hydroxy or methoxy; cyclohexyl or phenyl(C$_{1-2}$alkyl),
each R$_{7a}$ is independently hydrogen; methyl; ethyl; C$_{2-3}$alkyl monosubstituted by hydroxy or methoxy; cyclohexyl; phenyl or phenyl(C$_{1-2}$alkyl), or —NR$_{6a}$R$_{7a}$ is piperidino, morpholino, piperazino, N'-(C$_{1-4}$-alkyl)piperazino or N'-(amino-(CH$_2$)$_t$)piperazino, wherein t is 2 or 3;
each R$_{8a}$ and R$_{9a}$ is independently methyl or ethyl, and
R$_{10a}$ is methyl, ethyl or benzyl, or
—βNR$_{8a}$R$_{9a}$R$_{10a}$ is pyridinium, picolinium, lutidinium or

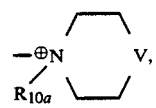

wherein
V is a direct bond, —CH$_2$—, —O—, —NH—, —N(C$_{1-4}$alkyl)-,

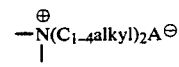

or —N((—CH$_2$)$_t$-NH$_2$)—,
wherein
t is 2 or 3, and
R$_{10a}$ is as defined above.
29. A compound according to claim 28 having the formula

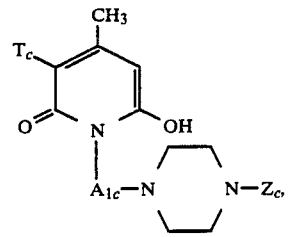

or an acid addition salt thereof,
wherein
A$_{1c}$ is linear or branched C$_{2-3}$alkylene,
T$_c$ is hydrogen, cyano or

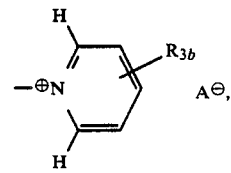

wherein
R$_{3b}$ is hydrogen or methyl,
Z$_c$ is

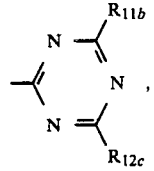

wherein
each of R$_{11b}$ and R$_{12c}$ is independently —NR$_{5a}$—A$_{2b}$—W$_b$, wherein
 $A_{2b}$ is linear $C_{2-3}$alkylene, and
 $W_b$ is $-NR_{6b}R_{7b}$ or $-\oplus NR_{8b}R_{9b}R_{10b}A\ominus$,
wherein
 each $R_{6b}$ and $R_{7b}$ is independently, hydrogen, methyl or ethyl,
 each $R_{8b}$ and $R_{9b}$ is methyl or ethyl, and
 $R_{10b}$ is methyl, ethyl or benzyl.
30. A compound or acid addition salt according to claim 29 wherein $T_c$ is hydrogen.
31. The compound according to claim 30 having the formula
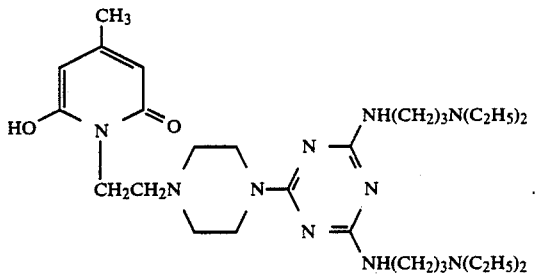
* * * * *